US 12,408,923 B2

(12) United States Patent
Rashidi

(10) Patent No.: US 12,408,923 B2
(45) Date of Patent: Sep. 9, 2025

(54) OCCLUSIVE DEVICES WITH THROMBOGENIC INSERTS

(71) Applicant: Covidien LP, Mansfield, MA (US)

(72) Inventor: Mehdi Rashidi, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 79 days.

(21) Appl. No.: 17/653,277

(22) Filed: Mar. 2, 2022

(65) Prior Publication Data

US 2023/0277184 A1 Sep. 7, 2023

(51) Int. Cl.
*A61B 17/12* (2006.01)

(52) U.S. Cl.
CPC .. *A61B 17/12113* (2013.01); *A61B 17/12177* (2013.01)

(58) Field of Classification Search
CPC ........ A61B 17/12113; A61B 17/12177; A61B 2017/1205; A61B 2090/3966; A61B 17/12031; A61B 17/12172
See application file for complete search history.

(56) References Cited

U.S. PATENT DOCUMENTS

| | | | |
|---|---|---|---|
| 2008/0281350 A1 | 11/2008 | Sepetka et al. | |
| 2014/0358178 A1* | 12/2014 | Hewitt | A61B 17/12172 606/200 |
| 2016/0249937 A1 | 9/2016 | Marchand et al. | |
| 2017/0245862 A1 | 8/2017 | Cox et al. | |
| 2017/0333046 A1* | 11/2017 | Roselli | A61B 17/12172 |
| 2018/0140305 A1* | 5/2018 | Connor | A61B 17/12118 |
| 2019/0343532 A1 | 11/2019 | Divino et al. | |
| 2020/0008870 A1* | 1/2020 | Gruba | A61B 18/082 |
| 2021/0007755 A1 | 1/2021 | Lorenzo et al. | |
| 2021/0068842 A1* | 3/2021 | Griffin | A61B 17/12122 |

\* cited by examiner

*Primary Examiner* — Kankindi Rwego
(74) *Attorney, Agent, or Firm* — Fortem IP LLP

(57) ABSTRACT

Devices for treating vascular defects and associated systems and methods are disclosed herein. In some embodiments, an occlusive device for treating an aneurysm includes an expandable mesh configured to span a neck of the aneurysm. The expandable mesh can include an upper wall and a lower wall. The occlusive device can also include an insert positioned within the expandable mesh between the upper and lower walls. The insert can have an inner surface and an outer surface. The inner surface of the insert can face the upper wall of the expandable mesh, and the outer surface of the insert can face the lower wall of the expandable mesh. The insert can be configured to promote thrombosis when the occlusive device is deployed within the aneurysm.

19 Claims, 10 Drawing Sheets

OCCLUSIVE DEVICES WITH THROMBOGENIC INSERTS

TECHNICAL FIELD

The present technology generally relates to medical devices, and in particular, to occlusive devices for treating vascular defects.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms with coil embolization involves packing the aneurysm sac with metal coils to reduce or disrupt the flow of blood into the aneurysm, thereby enabling a local thrombus or clot to form which fills and ultimately closes off the aneurysm. Although coiling has proven to have better outcomes than surgical clipping for both ruptured and unruptured aneurysms, treating complex aneurysms using conventional coiling is challenging. This is especially true for wide-necked aneurysms because coil segments may protrude from the aneurysm sac through the neck of the aneurysm and into the parent vessel, causing serious complications for the patient.

To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-necked aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual antiplatelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-necked, giant, fusiform, and blister-like aneurysms. However, because they are positioned in the parent vessel, flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have the potential to provide the intra-aneurysmal flow disruption of coiling with the definitive remodeling at the aneurysm-parent vessel interface achieved by intraluminal flow diverters. Endosaccular devices can be mesh devices configured to be deployed completely within the aneurysm sac, with the interstices of the mesh covering the aneurysm neck and reconstructing the aneurysm-parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

Accordingly, there is a need for improved devices, systems, and methods for treating aneurysms and other vascular defects.

SUMMARY

The subject technology is illustrated, for example, according to various aspects described below. These are provided as examples and do not limit the subject technology.

In one aspect of the present technology, an occlusive device for treating an aneurysm is provided. The occlusive device can include an expandable mesh configured to span a neck of the aneurysm, the expandable mesh including an upper wall and a lower wall. An internal cavity can be defined between the upper wall and the lower wall. The occlusive device can also include an insert positioned within the internal cavity of the expandable mesh between the upper wall and the lower wall, the insert including an inner surface and an outer surface. The inner surface of the insert can face the upper wall of the expandable mesh, and the outer surface of the insert can face the lower wall of the expandable mesh. The insert can be configured to promote thrombosis when the occlusive device is deployed within the aneurysm.

In some embodiments, when the occlusive device is deployed within the aneurysm, the expandable mesh forms a bowl structure including a distal portion, a proximal portion, and a cavity extending from the distal portion toward the proximal portion. The upper wall of the expandable mesh can form a concave surface defining the cavity of the bowl structure, and the lower wall of the expandable mesh can form the proximal portion of the bowl structure. When the occlusive device is deployed within the aneurysm, the insert can include a flared shape including a proximal end, and a distal end wider than the proximal end. The distal end of the insert can be positioned near and proximal to the distal portion of the bowl structure, and the proximal end of the insert can be positioned near and distal to the proximal portion of the bowl structure. The distal end of the insert can define a distal aperture and the concave surface of the bowl structure can be received at least partially within the distal aperture. The proximal end of the insert can define a proximal aperture configured to allow material to pass therethrough, or can be closed.

In some embodiments, the distal end of the bowl structure includes a plurality of mesh petals, each mesh petal being defined by a distal end of the upper wall and a distal end of the lower wall of the expandable mesh, and each mesh petal including a distal end sub-cavity between the distal end of the upper wall and the distal end of the lower wall. The distal end sub-cavity can be connected to the internal cavity of the expandable mesh. The distal end of the insert can include a plurality of insert petals. The number of insert petals can be the same as the number of mesh petals. Each insert petal can be radially aligned with and positioned at least partially within the distal end sub-cavity of a corresponding mesh petal.

In some embodiments, the expandable mesh includes a braid.

In some embodiments, the insert includes a polymeric material. The polymeric material can be expanded polytetrafluoroethylene.

In some embodiments, the insert includes a metallic material. The metallic material can be Cobalt Chromium.

In some embodiments, the insert defines a plurality of pores extending between the inner surface and the outer surface of the insert. The plurality of pores can be configured to enhance thrombogenicity of the insert. The plurality of pores can define an average diameter within a range from 10 microns to 300 microns.

In some embodiments, the insert includes texturing on one or more of the inner surface or the outer surface of the insert. The texturing can be configured to enhance thrombogenicity of the insert.

In some embodiments, the insert includes a mesh.

In some embodiments, the insert is configured to release at least one active agent into the aneurysm. The at least one active agent can be configured to promote thrombosis within the aneurysm. The at least one active agent can be incorporated into a first coating on at least one surface of the insert. The first coating can include the at least one active agent combined with a polymeric material. Optionally, the at least one active agent can be incorporated into a bulk material of the insert. The at least one active agent can include a pharmaceutical compound, a protein, a peptide, an antibody, a nucleic acid, a cell, or a particle.

In some embodiments, the insert includes a first portion configured to release a first active agent, and a second portion configured to release a second active agent. The first portion can be the inner surface of the insert, and the second portion can be the outer surface of the insert. The first active agent can be configured to promote thrombosis, and the second active agent can be configured to promote endothelialization.

In some embodiments, the occlusive device further includes a second coating on a portion of the lower wall of the expandable mesh. The second coating can be configured to reduce thrombogenesis on the portion of the lower wall. The second coating can be configured to enhance endothelialization on the portion of the lower wall.

In some embodiments, the occlusive device further includes a hub coupled to the lower wall of the expandable mesh. The hub can include a detachment element configured to releasably couple the expandable mesh to a pusher member.

In another aspect of the present technology, an occlusive device for treating an aneurysm is provided. The occlusive device can include a mesh configured to self-expand into a bowl structure, the mesh including a distal layer and a proximal layer. The distal layer can include a concave surface defining a cavity of the bowl structure. The occlusive device can further include an insert positioned within the mesh between the distal layer and the proximal layer. The insert can include an outer surface and an inner surface. The insert can include at least one thrombogenic feature.

In some embodiments, when the occlusive device is deployed within the aneurysm, the mesh covers a neck of the aneurysm and the cavity faces a dome of the aneurysm.

In some embodiments, the mesh includes a fold region between the distal and proximal layers.

In some embodiments, the outer surface of the insert is oriented toward the proximal layer of the mesh, and the inner surface of the insert is oriented toward the distal layer of the mesh.

In some embodiments, the insert includes a flared shape including a wider distal end and a narrower proximal end. The wider distal end of the insert can be positioned near and proximal to the distal layer of the mesh, and the narrower proximal end of the insert can be positioned near and distal to the proximal layer of the mesh. The wider distal end of the insert can define a distal aperture and the concave surface of the mesh can be received at least partially within the distal aperture. The narrower proximal end of the insert can include a proximal aperture configured to allow material to pass therethrough, or can be closed.

In some embodiments, the mesh includes a braid.

In some embodiments, the at least one thrombogenic feature includes a thrombogenic material. The thrombogenic material can include a polymeric material, a metallic material, or a combination thereof.

In some embodiments, the at least one thrombogenic feature includes a plurality of pores extending between the inner surface and the outer surface of the insert. The plurality of pores can be configured to enhance thrombogenicity of the insert. The plurality of pores can define an average diameter within a range from 0.1 microns to 1000 microns.

In some embodiments, the at least one thrombogenic feature includes texturing on one or more of the inner surface or the outer surface of the insert, wherein the texturing is configured to enhance thrombogenicity of the insert.

In some embodiments, the at least one thrombogenic feature includes a plurality of filaments.

In some embodiments, the at least one thrombogenic feature includes a releasable agent. The releasable agent can be incorporated into a first coating on one or more of the outer surface or the inner surface of the insert. The releasable agent can be incorporated into a bulk material of the insert.

In some embodiments, the occlusive device further includes a second coating on a portion of the proximal layer of the mesh. The second coating can be configured to reduce thrombogenesis on the portion of the proximal layer. The second coating can be configured to enhance endothelialization on the portion of the proximal layer.

In some embodiments, the occlusive device further includes a hub coupled to the proximal layer of the mesh. The hub can include a detachment element configured to releasably couple the mesh to a pusher member.

In a further aspect of the present technology, an occlusive device for treating an aneurysm is provided. The occlusive device can include an expandable mesh configured to span a neck of the aneurysm, the expandable mesh including a distal wall and a proximal wall. The occlusive device can also include an insert positioned between the distal wall and the proximal wall the insert being formed from a continuous material having an inner surface and an outer surface. The insert can include at least one thrombogenic feature.

In some embodiments, the inner surface of the insert faces the distal wall of the expandable mesh, and the outer surface of the insert faces the proximal wall of the expandable mesh.

In some embodiments, when the occlusive device is deployed within the aneurysm, the proximal wall of the expandable mesh covers the neck of the aneurysm. When the occlusive device is deployed within the aneurysm, the expandable mesh can form a bowl structure having a distal portion, a proximal portion, and a cavity extending from the distal portion toward the proximal portion. The distal wall of the expandable mesh can form a concave surface defining the cavity of the bowl structure, and the proximal wall of the expandable mesh can form the proximal portion of the bowl structure. When the occlusive device is deployed within the aneurysm, the insert can have a flared shape with a distal end and a proximal end, the distal end being wider than the proximal end. The distal end of the insert can be positioned near and proximal to the distal portion of the bowl structure, and the proximal end of the insert can be positioned near and distal to the proximal portion of the bowl structure.

In some embodiments, the distal portion of the bowl structure includes a plurality of first flanges. Each first flange can be defined by a distal end of the distal wall and a distal end of the proximal wall of the expandable mesh. Each first flange can include an internal cavity between the distal end of the distal wall and the distal end of the proximal wall. The distal end of the insert can include a plurality of second flanges. The number of second flanges can be the same as the number of first flanges. Each second flange can be radially aligned with and positioned at least partially within the internal cavity of a corresponding first flange In some embodiments, the expandable mesh includes an annular ridge connecting the distal wall and the proximal wall, the annular ridge defining a distal lip of the expandable mesh. The annular ridge can have a rounded shape configured to avoid tissue damage when the expandable mesh is introduced into the aneurysm.

In some embodiments, the continuous material includes a thrombogenic material, and the at least one thrombogenic feature includes the thrombogenic material. The thrombogenic material can include a polymeric material, a metallic material, or a combination thereof. The continuous material of the insert can include a substrate extending between the inner surface and the outer surface of the insert, and the thrombogenic material can include a thrombogenic agent immobilized on the substrate.

In some embodiments, the at least one thrombogenic feature includes a physical structure formed in the continuous material of the insert. The physical structure can include pores, texturing, protrusions, indentations, or a combination thereof.

In some embodiments, the at least one thrombogenic feature includes a releasable thrombogenic agent. The releasable thrombogenic agent can be incorporated into a coating on one or more of the inner surface or the outer surface of the insert. The releasable thrombogenic agent can be incorporated into the continuous material of the insert.

In some embodiments, the occlusive device further includes an anti-thrombogenic coating on a portion of the proximal wall of the expandable mesh. The occlusive device can also include a hub coupled to the proximal wall of the expandable mesh. The anti-thrombogenic coating can cover at least a portion of the hub.

In another aspect of the present technology, a method of treating an aneurysm is provided. The method can include positioning an occlusive device within the aneurysm. The occlusive device can include a distal mesh layer oriented toward a dome of the aneurysm, a proximal mesh layer covering a neck of the aneurysm, and an insert positioned between the distal mesh layer and the proximal mesh layer, the insert including an inner surface facing the distal mesh layer, and an outer surface facing the proximal mesh layer.

The method can also include promoting thrombogenesis within the aneurysm via at least one thrombogenic feature of the insert.

In some embodiments, the method further includes introducing the occlusive device into the aneurysm via an elongate shaft. The occlusive device can be disposed within the elongate shaft in a low-profile configuration. Introducing the occlusive device can include advancing the occlusive device out of the elongate shaft such that the occlusive device self-expands into an expanded configuration. When the occlusive device is in the expanded configuration, the distal mesh layer can include a concave shape forming a cavity facing the dome of the aneurysm. The insert can include a flared shape with a wider distal end oriented toward the dome of the aneurysm and a narrower proximal end oriented toward the neck of the aneurysm.

In some embodiments, the least one thrombogenic feature includes a plurality of pores extending between the inner surface and the outer surface of the insert, the plurality of pores being configured to enhance thrombogenicity of the insert.

In some embodiments, the at least one thrombogenic feature includes texturing on one or more of the inner surface or the outer surface of the insert, the texturing being configured to enhance thrombogenicity of the insert.

In some embodiments, the at least one thrombogenic feature includes a plurality of filaments.

In some embodiments, the at least one thrombogenic feature includes an active agent on or within the insert. The method can further include releasing the active agent from the insert into the aneurysm. Optionally, the method can also include releasing a second active agent from the insert into the aneurysm, the second active agent being different from the active agent. The active agent can be released from a first coating on the inner surface of the insert, and the second active agent can be released from a second coating on the outer surface of the insert.

In some embodiments, the method further includes inhibiting thrombogenesis on a portion of the proximal mesh layer of the occlusive device.

In some embodiments, the method further includes promoting endothelialization on a portion of the proximal mesh layer of the occlusive device.

In some embodiments, the method further includes detaching the occlusive device from a pusher member.

In some embodiments, the method further includes introducing an embolization element into the aneurysm. The embolization element can include a liquid embolic or a coil. The insert can include a lumen, and the embolization element can be introduced into the aneurysm via the lumen. The method can also include retaining the embolization element within the aneurysm via the occlusive device.

Additional features and advantages of the present technology will be set forth in the description below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
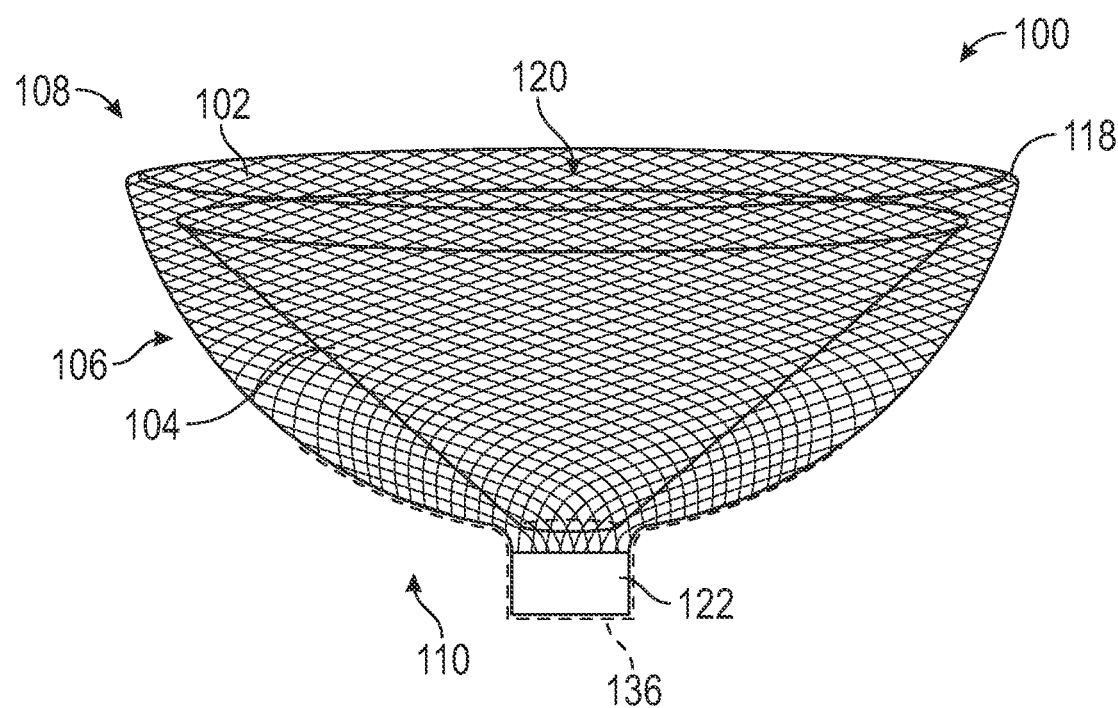
FIG. 1A is a perspective view of an occlusive device configured in accordance with embodiments of the present technology.

The present technology relates to devices for treating vascular defects such as aneurysms, and associated systems and methods. In some embodiments, for example, an occlusive device for treating an aneurysm includes an expandable mesh configured to span a neck of the aneurysm. The expandable mesh can be a multilayered structure including an upper wall and a lower wall, with the upper wall oriented toward the aneurysm dome and the lower wall extending across the aneurysm neck. The occlusive device also includes an insert positioned within the expandable mesh between the upper and lower walls. The insert can include at least one feature configured to promote thrombosis when implanted in the aneurysm, referred to herein as a "thrombogenic feature." For example, the thrombogenic feature can include any of the following: (a) physical structures (e.g., pores, indentations, protrusions, texturing, filaments) that increase the blood-contacting surface area of the insert and/or disrupt blood flow near the insert; (b) a thrombogenic material (e.g., expanded polytetrafluoroethylene, Cobalt Chromium); and/or (c) a releasable thrombogenic agent that elutes from the insert into the aneurysm cavity. Accordingly, the occlusive device can promote faster filling and healing of the aneurysm, either as a standalone device or in combination with an embolization element (e.g., a liquid embolic or coil).

Optionally, the occlusive device can be configured to reduce or inhibit thrombosis at locations that pose an embolism risk. For example, the portion of the lower wall of the expandable mesh that spans the neck of the aneurysm can be coated with an anti-thrombogenic material to reduce the likelihood of clot formation. Alternatively or in combination, the insert can be configured to elute an active agent toward the aneurysm neck to inhibit thrombosis and/or promote endothelialization at the neck. This approach can improve the safety of the treatment procedure, as well as enhance the natural healing response.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," and "lower" can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

Figure 1B:
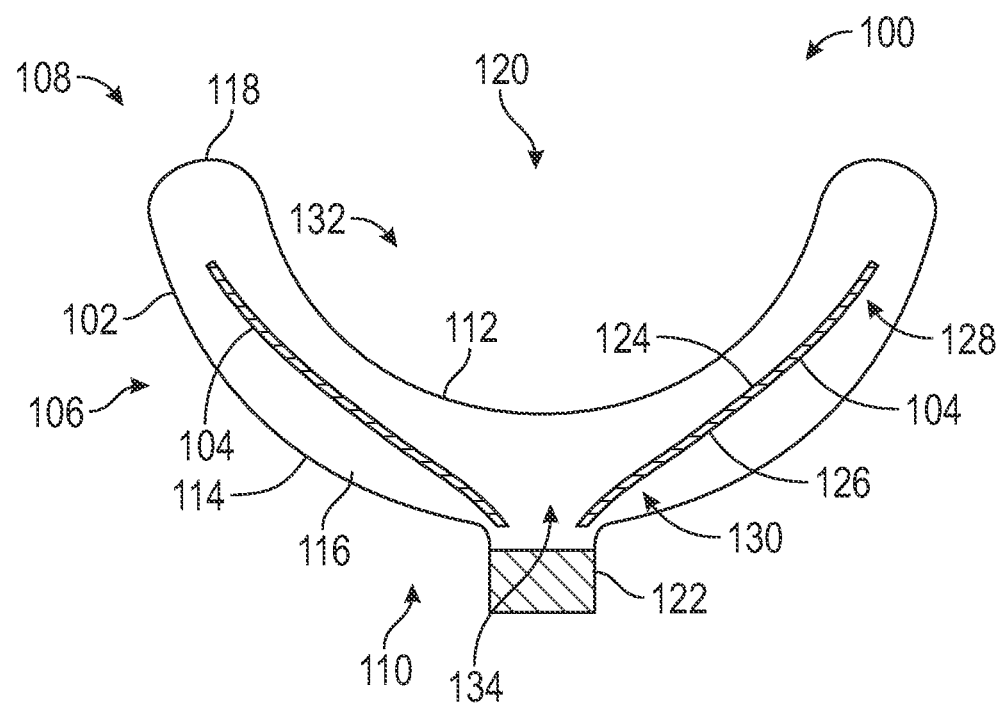
FIG. 1B is a side cross-sectional view of the occlusive device of FIG. 1A.

FIGS. 1A-1D illustrate an occlusive device 100 ("device 100") configured in accordance with embodiments of the present technology. Referring first to FIGS. 1A and 1B together, which are perspective and side cross-sectional views of the device 100, respectively, the device 100 includes a mesh 102 enclosing an insert 104. The mesh 102 is configured to be deployed within an aneurysm sac to reduce or prevent blood flow from the parent vessel into the aneurysm sac, and/or provide a scaffold for endothelial cell attachment, while the insert 104 is configured to promote thrombosis within the aneurysm sac to fill the interior space. The growth and development of an endothelial layer over the aneurysm neck can wall off the aneurysm from the parent vessel and allow flow dynamics to equilibrate at the defect. Upon endothelialization, the fluid pressure can be evenly distributed along the parent vessel in a manner that inhibits recanalization at the defect post-treatment. Moreover, blood from within the parent vessel no longer has access to the walled-off defect once the endothelialization process is complete and/or the interior of the aneurysm has been occluded by the device 100 and clot material. The device 100 can be used as a standalone device, or can be used to retain an embolization element (e.g., an embolic liquid or coil) within the aneurysm and prevent prolapse into the parent vessel. Accordingly, the device 100 can facilitate healing of the defect and/or prevent recanalization.

The mesh 102 includes an annular body 106 configured to be positioned within the aneurysm sac, a distal portion 108 configured to be oriented toward the aneurysm dome, and a proximal portion 110 configured to cover the aneurysm neck. As best seen in FIG. 1B, the body 106 of the mesh 102 can be a hollow structure including an upper wall 112 (e.g., an upper and/or distal mesh layer), a lower wall 114 (e.g., a lower and/or proximal mesh layer), and an internal cavity 116 defined between the upper wall 112 and lower wall 114. In some embodiments, the upper wall 112 is curved toward the lower wall 114, such that the upper wall 112 and lower wall 114 are connected to each other via a fold region 118. Thus, the fold region 118 can constitute the distal portion 108 of the mesh 102, and the lower wall 114 can constitute the proximal portion 110 of the mesh 102. In other embodiments, however, the upper wall 112 can be vertically aligned with the fold region 118, or can be curved away from the lower wall 114, such that the upper wall 112 constitutes the distal portion 108 of the mesh 102.

In some embodiments, the mesh 102 is an expandable element that is configured to transform from a low-profile (e.g., compressed and/or constrained) configuration for delivery to the aneurysm within an elongate shaft (e.g., a delivery catheter), and an expanded configuration (shown in FIGS. 1A and 1B) for deployment within the aneurysm. The mesh 102 can be formed of a resilient material and shape set such that, when unconstrained, the mesh 102 self-expands to a predetermined shape that conforms to the interior of the aneurysm. For example, in the illustrated embodiment, the mesh 102 forms a bowl structure when expanded. The upper wall 112 of the mesh 102 can serve as the inner concave surface of the bowl structure and can define a cavity 120 extending from the distal portion 108 toward the proximal portion 110. The cavity 120 can have a hemispherical, hemi-ellipsoidal, or other suitable shape for receiving and retaining an embolization element within the aneurysm, as described further below. The lower wall 114 can serve as the outer convex surface of the bowl structure and can be configured to apply an outward force against the walls of the aneurysm upon deployment to secure the mesh 102 within the aneurysm. The fold region 118 can form an annular ridge extending circumferentially around the cavity 120 to serve as the distal lip of the bowl structure. The fold region 118 can have a rounded, atraumatic shape to avoid tissue damage when introducing the mesh 102 into the aneurysm.

In other embodiments, however, the mesh 102 can assume a different shape when expanded. Examples of other suitable shapes include, but are not limited to, tubes, cylinders, hemispheres, polyhedrons (e.g., cuboids, tetrahedrons (such as pyramids), octahedrons, prisms), prolate spheroids, oblate spheroids, ovoids, plates (e.g., discs, polygonal plates), non-spherical surfaces of revolution (e.g., toruses, cones, cylinders, or other shapes rotated about a center point or a coplanar axis), or combinations thereof. In such embodiments, the configuration of the upper wall 112, lower wall 114, and fold region 118 described herein can be modified as appropriate to form the desired shape. For example, in embodiments where the mesh 102 has a spheroid or ovoid shape, the upper wall 112 can form a convex surface that is curved away from the lower wall 114, and the fold region 118 can be omitted.

In some embodiments, the mesh 102 is a braid formed of a plurality of braided or woven filaments (e.g., metal wires, polymer wires, or both). For example, the mesh 102 can be formed of 24, 32, 36, 48, 64, 72, 96, 128, or 144 filaments. The filaments can have shape memory and/or superelastic properties, such that the mesh 102 can be heat-set to assume the predetermined shape when released from the constraints of the elongate shaft. In some embodiments, some or all of the filaments (e.g., at least 25%, 50%, 80%, or 100% of the filaments) are made of one or more shape memory and/or superelastic materials (e.g., Nitinol). The filaments can have any suitable size, such as a diameter within a range from 0.0004 inches to 0.0020 inches, or from 0.0009 inches to 0.0012 inches. For example, some or all of the filaments can have a diameter of no more than 0.0004 inches, 0.0005 inches, 0.0006 inches, 0.0007 inches, 0.0008 inches, 0.0009 inches, 0.001 inches, 0.0011 inches, 0.0012 inches, 0.0013 inches, 0.0014 inches, 0.0015 inches, 0.0016 inches, 0.0017 inches, 0.0018 inches, 0.0019 inches, or 0.0020 inches. Some or all of the filaments of the mesh 102 can have the same diameter, or some or all of the filaments can have different cross-sectional diameters. For example, some of the filaments can have a slightly thicker diameter to impart additional strength to the mesh 102. The thicker filaments can impart greater strength to the mesh 102 without significantly increasing the delivery profile of the device 100, while the thinner wires can offer some strength while filling out the matrix density of the mesh 102. In other embodiments, however, the mesh 102 can be a non-braided structure, such as a stent, and the filaments can instead be formed via laser-cutting, etching, or other suitable techniques known to those of skill in the art.

The proximal portion 110 of the mesh 102 can be coupled to a hub 122. The hub 122 can be a collar, band, ring, etc., that crimps the filaments of the mesh 102 together. The hub 122 can include or be connected to a detachment element (not shown) that releasably couples the device 100 to a pusher member. The pusher member can be an elongate rod, shaft, wire, etc., that is configured to push the device 100 through a distal end of a delivery catheter to deploy the device 100 within the aneurysm, as described further below. Optionally, the pusher member can also be used to pull the device 100 partially or fully back into the delivery catheter, e.g., for repositioning purposes. The detachment element can utilize any suitable detachment technique known to those of skill in the art, such as electrolytic detachment, mechanical detachment, thermal detachment, electromagnetic detachment, or combinations thereof. An example of a detachment element suitable for use with the present technology is the Axium™ or Axium™ Prime Detachable Coil System (Medtronic).

Figure 1C:
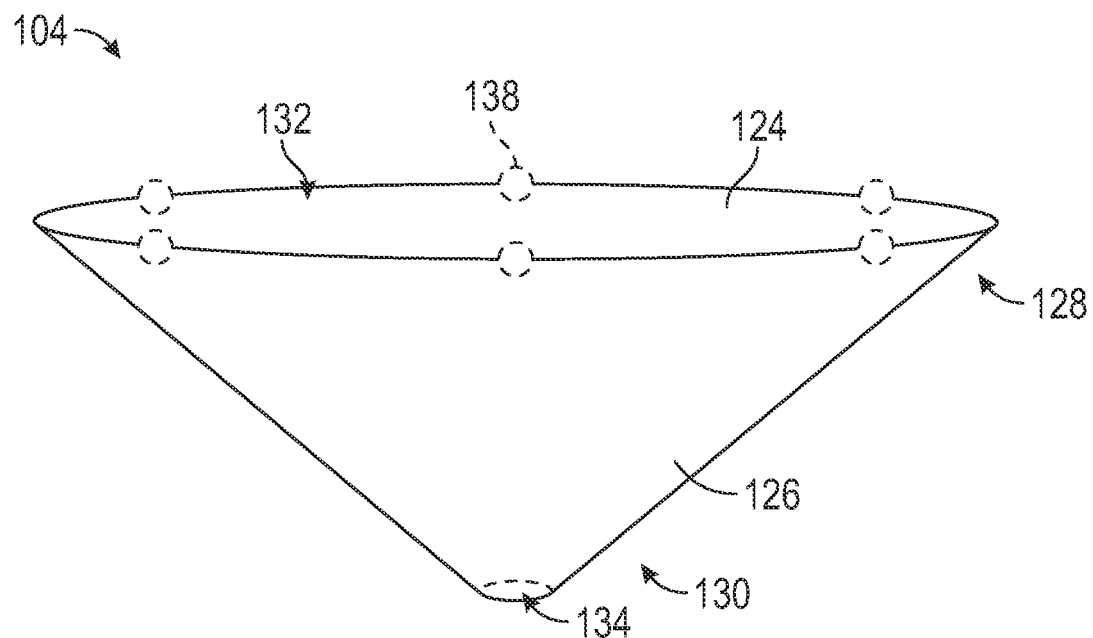
FIG. 1C is a perspective view of an insert of the occlusive device of FIG. 1A.

The insert 104 is positioned within the mesh 102 in the internal cavity 116 between the upper wall 112 and lower wall 114. As best seen in FIG. 1C, which shows a perspective view of the insert 104, the insert 104 includes a flattened element (e.g., a sheet, film, strip, mesh, membrane, etc.) that is formed into a three-dimensional structure having an inner surface 124, an outer surface 126, a distal end 128, and a proximal end 130. The insert 104 can conform to the shape of the internal cavity 116 of the mesh 102, with the inner surface 124 of the insert 104 facing the upper wall 112 of the mesh 102, the outer surface 126 of the insert 104 facing the lower wall 114 of the mesh 102, the distal end 128 of the insert 104 positioned near the distal portion 108 of the mesh 102, and the proximal end 130 of the insert 104 positioned near the proximal portion 110 of the mesh 102. The proximal end 130 of the insert 104 can be positioned distal to the hub 122, or can extend at least partially into the lumen of the hub 122 and/or can be attached to the hub 122. In some embodiments, the insert 104 is encapsulated within the mesh 102 but is not attached to the mesh 102, e.g., the distal end 128 and proximal end 130 of the insert 104 remain free. Alternatively, the insert 104 can be affixed to the mesh 102 at one or both ends via adhesives, welding, bonding, fasteners, etc.

In the illustrated embodiment, because the mesh 102 is bowl-shaped with a wider distal portion 108 and a narrower proximal portion 110, the insert 104 also has a flared (e.g., conical or bowl-like) shape with a wider distal end 128 and a narrower proximal end 130. The flared shape can be advantageous for conforming to the geometry of the mesh 102, as well as for promoting directional release of active agents from the insert 104, as described further below. In other embodiments, however, depending on the shape of the mesh 102, the distal end 128 can be narrower than the proximal end 130, or can have the same width as the proximal end 130. Additionally, the insert 104 can have a different shape than the flared shape shown in FIGS. 1A-1D, including, but not limited to, tubes, cylinders, hemispheres, polyhedrons, spheroids, ovoids, plates, toruses, etc.

Figure 1D:
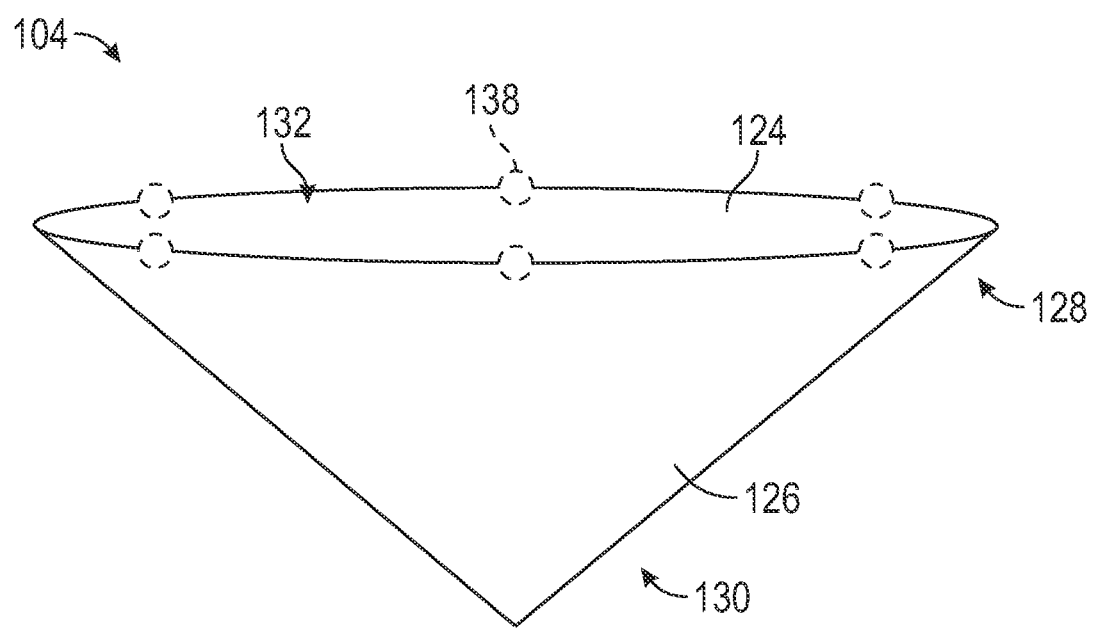
FIG. 1D is a perspective of another embodiment of the insert of FIG. 1C.

The insert 104 can include at least one opening exposing the inner surface 124 for interactions with materials within the aneurysm sac. For example, the distal end 128 of the insert 104 can define a distal aperture 132 to provide a passageway for blood to contact the inner surface 124 and/or for active agents released from the inner surface 124 to elute into the aneurysm cavity, as described further below. The distal aperture 132 can also receive and surround the concave portion of the upper wall 112 of the mesh 102, such that the cavity 120 of the mesh 102 extends at least partially into the insert 104. The proximal end 130 can also define a proximal aperture 134 (FIG. 1C) that forms a lumen enabling material (e.g., blood, a liquid embolic) to pass through, as discussed further below. In other embodiments, however, the distal end 128 and/or proximal end 130 of the insert 104 can be closed. For example, FIG. 1D illustrates another embodiment of the insert 104 in which the proximal end 130 does not include the proximal aperture 134. This configuration can be advantageous for controlling the directional release of active agents eluting from the inner surface 124 (e.g., to inhibit elution out of the aneurysm and into the parent vessel), as described further detail below.

In some embodiments, the insert 104 includes at least one thrombogenic feature configured to promote thrombosis within the aneurysm sac. For example, the thrombogenic feature can be a physical structure of the insert 104 that promotes blood coagulation on and/or near the insert 104. In some embodiments, the physical structure increases the surface area of the insert 104, which can enhance thrombosis by providing more exposed surfaces for interaction with blood components (e.g., via physical adsorption and/or chemical bonding). Alternatively or in combination, the physical structure can disrupt blood flow through and/or near the insert 104, which can promote hemostasis and coagulation. Examples of thrombogenic physical structures include, but are not limited to, pores, texturing, protrusions (e.g., bumps, ridges), indentations (e.g., recesses, grooves), and/or woven or braided filaments, and are described further below with respect to FIGS. 2A-2D.

As another example, the insert 104 can be made partially or entirely of a material having thrombogenic properties, such that the material itself is the thrombogenic feature. The material can be a polymeric material, a metallic material, or a suitable combination thereof. Examples of thrombogenic materials include, but are not limited to, expanded polytetrafluoroethylene (ePTFE), etched polytetrafluoroethylene, polyurethane, polycarbonate, polyester (e.g., Dacron), polylactic acid, polyglycolic acid, polyolefin, Parylene, silicone, Cobalt Chromium (CoCr), Platinum, Tungsten, stainless steel, Nitinol, fibrin, fibronectin, gelatin, collagen, alginate, chitin, chitosan, cellulose, methylcellulose, silk, poly-N-acetylglucosamine, or combinations (e.g., mixtures, copolymers, alloys) thereof. Optionally, the thrombogenic material can include a substrate (e.g., a polymer or a metal) that has been modified with an immobilized thrombogenic agent. For example, thrombogenic agents can be applied to the surface of the substrate via coating (e.g., spray coating, dip coating, spin coating), chemical crosslinking, adsorption, deposition (e.g., chemical vapor deposition, plasma vapor deposition), or other suitable techniques known to those of skill in the art. Examples of thrombogenic agents include any of the thrombogenic materials listed above, as well as coagulation factors (e.g., prothrombin, thrombin, fibrinogen, fibrin, Factor V, Factor Va, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, tissue factor, von Willebrand factor, platelet activating factor, plasminogen activator inhibitor 1 (PAI-1)), anti-fibrinolytic agents (e.g., tranexamic acid, aminocaproic acid, aprotinin, pepstatin, leupeptin, antipain, chymostatin, gabexate), or combinations thereof. The substrate itself can also have thrombogenic properties, or can be made of a non-thrombogenic material.

In a further example, the thrombogenic feature can be a releasable thrombogenic agent that is incorporated into the insert 104. The releasable thrombogenic agent can be or include any of the thrombogenic agents previously described herein (e.g., coagulation factors, anti-fibrinolytic agents, etc.). When the insert 104 is implanted within the aneurysm, the thrombogenic agent can elute out of the insert 104 and into the surrounding physiological environment to promote coagulation within the aneurysm sac. The thrombogenic agent can be incorporated into the insert 104 using various techniques. For example, the thrombogenic agent can be encapsulated or otherwise contained in a controlled release coating applied to the inner surface 124 and/or outer surface 126 of the insert 104. Alternatively or in combination, the thrombogenic agent can be incorporated into the bulk material of the insert 104, with the bulk material being configured for controlled release of the thrombogenic agent.

Optionally, the insert 104 can be configured to release other types of active agents into the surrounding environment, in addition or alternatively to the thrombogenic agent. For example, the active agent can promote healing and/or endothelialization on or near the device 100. The active agent can be encapsulated or otherwise contained in a controlled release coating applied to the inner surface 124 and/or outer surface 126 of the insert 104. Alternatively or in combination, the active agent can be incorporated into the bulk material of the insert 104, with the bulk material being configured for controlled release of the active agent. Additional examples and details of techniques for achieving controlled release of thrombogenic agents and other active agents from the insert 104 are described below with respect to FIGS. 3A-3C.

In some embodiments, one or more sections of the device 100 include a coating 136 configured to inhibit thrombogenesis. For example, when the device 100 is deployed within the aneurysm, certain components may protrude into the parent vessel and/or be exposed to blood flow from the parent vessel, such as the proximal portion 110 of the mesh 102 and/or the hub 122. Accordingly, these components can include an anti-thrombogenic coating 136 (FIG. 1A) configured to improve hemocompatibility and reduce thrombogenic surface activity. For example, the coating 136 can include a phosphorylcholine compound, such as Shield Technology™ (Medtronic). Additional examples of hemocompatible materials that can be used for the coating 136 include, but are not limited to, heparin, albumin, poly (ethylene oxide), immobilized and/or releasable anti-thrombogenic agents (e.g., direct thrombin inhibitors, anti-platelet agents, urokinase, tissue plasminogen activator (t-PA)), or combinations thereof. In some embodiments, the anti-thrombogenic coating 136 is localized only to those portions of the device 100 that are exposed to and/or near the parent vessel, and the remaining portions of the device 100 do not include any anti-thrombogenic coating.

Optionally, the device 100 can include at least one coating that performs other functions, such as promoting endothelialization and/or healing (e.g., via incorporation of immobilized and/or releasable vascular endothelial growth factor (VEGF), RGD peptide, etc.). The coating can alternatively or additionally increase lubricity to reduce the force needed to push the device 100 through the delivery catheter and/or withdraw the device 100 into the delivery catheter. The coating may be the same as the coating 136 (e.g., the coating 136 exhibits other properties in addition to anti-thrombogenic properties), or can be a different coating (e.g., another coating layered on top of or below the coating 136, or on a different portion of the device 100).

In some embodiments, the device 100 includes one or more radiopaque components to facilitate visualization. For example, some or all of the filaments of the mesh 102 can be drawn-filled tubes ("DFT") having a radiopaque core (e.g., Platinum) surrounded by a shape memory alloy and/or superelastic alloy (e.g., Nitinol, CoCr, etc.). As another example, the insert 104 can include one or more radiopaque markers 138 (FIG. 1C), such as radiopaque beads, discs, wires, etc. The radiopaque markers 138 can be located on the outer surface 126 and/or the inner surface 124 of the insert 104. Optionally, the radiopaque markers 138 can protrude outward from the surface(s) of the insert 104 to promote thrombogenesis via disruption of blood flow, as described elsewhere herein. Although the radiopaque markers 138 are depicted as being distributed around the periphery of the distal end 128 of the insert 104, the radiopaque markers 138 can alternatively or additionally be located at other portions of the insert 104, such as at the proximal end 130, or at an intermediate region spaced apart from the distal end 128 and proximal end 130. Optionally, radiopaque markers can alternatively or additionally be located at or near the hub 122, on the mesh 102, and/or any other suitable portion of the device 100.

The device 100 can be manufactured using various techniques. For example, the mesh 102 can be formed from a braid or stent that is wrapped around a mold and heat set into the desired shape. If any coatings are used (e.g., coating 136), the coating(s) can be applied to the specified portion(s) of the mesh 102 via dipping, spraying, deposition, etc., either before or after the mesh 102 has been shaped. The insert 104 can be fabricated separately by forming a substrate (e.g., a film, sheet, strip, mesh, membrane) into the desired shape. Optionally, in embodiments where the insert 104 is made from a shape memory material, the insert 104 can be heat set into the desired shape. In some embodiments, the substrate already has thrombogenic properties, e.g., the substrate already includes thrombogenic physical features and/or is made of a thrombogenic material. Alternatively or in combination, the substrate can be modified to include thrombogenic properties, such as by adding thrombogenic physical features (e.g., via etching, cutting, abrading), and/or by adding immobilized and/or releasable thrombogenic agents (e.g., by coating, deposition, crosslinking). The modifications to the substrate can be made before and/or after forming the substrate into the desired shape for the insert 104.

In some embodiments, the device 100 is assembled by placing the insert 104 into the mesh 102, after the mesh 102 has been heat set into the desired shape. Alternatively, the insert 104 can be placed into the mesh 102 before the mesh 102 has been heat set. In such embodiments, the heat setting process can be performed at a sufficiently low temperature to avoid degrading any active agents that are incorporated into the insert 104. Once the insert 104 is positioned within the mesh 102, the proximal portion 110 of the mesh 102 can be crimped together via the hub 122 to enclose and secure the insert 104.

FIGS. 2A-2D illustrate representative examples of thrombogenic physical features that may be incorporated into the insert 104 of FIGS. 1A-1D, in accordance with embodiments of the present technology. Any of the embodiments described in connection with FIGS. 2A-2D can be combined with each other and/or incorporated into any of the devices described herein.

Figure 2A:
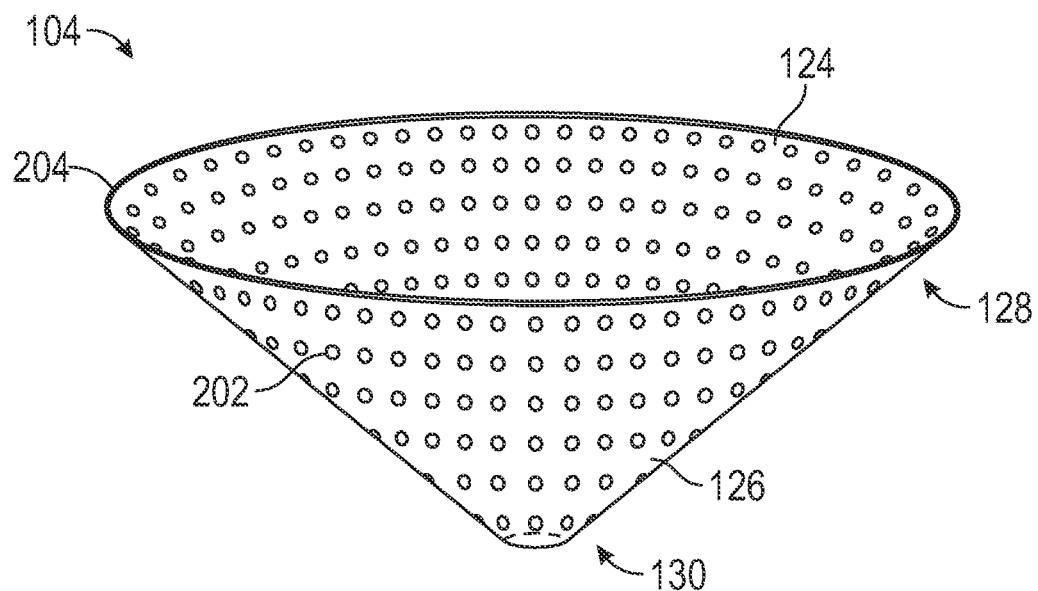
FIG. 2A is a perspective view of an insert including a plurality of pores, in accordance with embodiments of the present technology.

FIG. 2A is a perspective view of an insert 104 including a plurality of pores 202 configured to promote thrombosis, in accordance with embodiments of the present technology. The pores 202 can be formed in a substrate 204 (e.g., a continuous material such as a film, strip, sheet, membrane, etc.) via laser-cutting, etching, punching, or other suitable techniques. Alternatively or in combination, the substrate 204 itself can be made of a porous material (e.g., a polymeric material such as ePTFE), such that no additional process steps are needed to form the pores 202. The pores 202 can have any suitable geometry (e.g., size, shape). For example, the average diameter of the pores 202 can be within a range from 0.1 µm to 1000 µm, such as from 10 µm to 300 µm. In some embodiments, the average diameter can be less than or equal to 1000 µm, 900 µm, 800 µm, 700 µm, 600 µm, 500 µm, 400 µm, 300 µm, 200 µm, 100 µm, 90 µm, 80 µm, 70 µm, 60 µm, 50 µm, 40 µm, 30 µm, 20 µm, 10 µm, or 5 µm. The pores 202 can be circular, oval, triangular, square, rectangular, diamond-shaped, polygonal, or any other regular or irregular shape, and can extend between the inner surface 124 and outer surface 126 of the insert 104. Although the pores 202 are depicted in FIG. 2A as having a uniform geometry (e.g., size, shape), in other embodiments, some or all of the pores 202 can have different geometries. Additionally, although the pores 202 are shown as being evenly distributed across the inner surface 124 and outer surface 126 of the insert 104, the pores 202 can alternatively be localized to certain portions of the insert 104, such as at or near the distal end 128 of the insert 104, at or near the proximal end 130 of the insert 104, at an intermediate region of the insert 104 that is spaced apart from the distal end 128 and/or proximal end 130, etc. Moreover, although the pores 202 are depicted as being arranged in a series of circumferential rows, in other embodiments, the pores 202 can be arranged in a different pattern or can be randomly distributed.

Figure 2B:
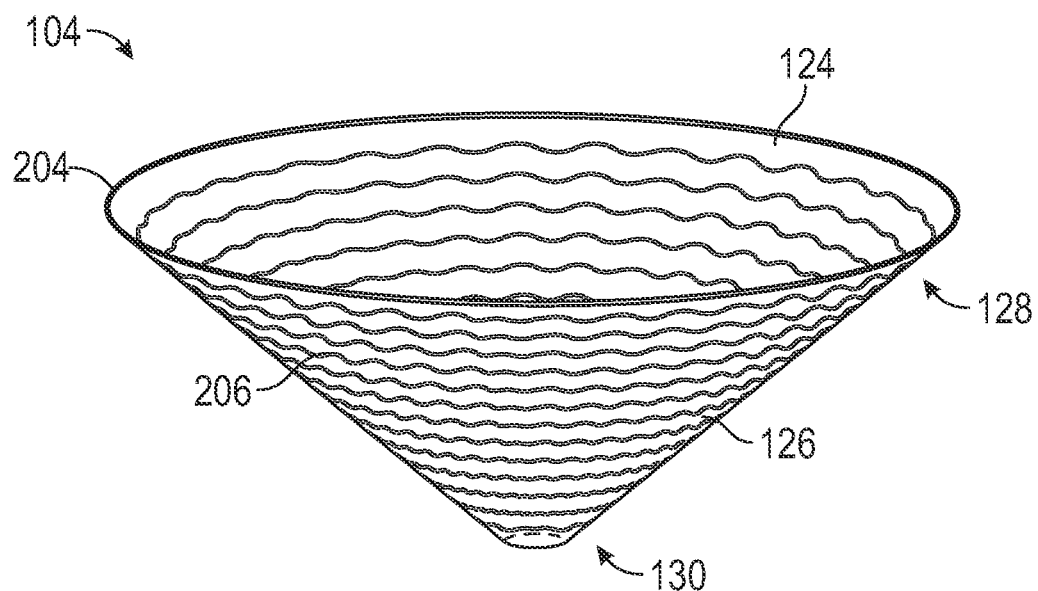
FIG. 2B is a perspective view of an insert including a plurality of grooves, in accordance with embodiments of the present technology.

FIG. 2B is a perspective view of an insert 104 including a plurality of grooves 206 configured to promote thrombosis, in accordance with embodiments of the present technology. The grooves 206 can be formed in a substrate 204 (e.g., a continuous material such as a film, strip, sheet, etc.) via etching, cutting, or other suitable techniques. The grooves 206 can have any suitable geometry. For example, although the grooves 206 are illustrated as having an undulating and/or serpentine shape, in other embodiments, some or all of the grooves 206 can have a different shape, such as a zigzag shape, a linear shape, a curvilinear shape, etc. The grooves 206 can be annular structures that extend around the entire circumference of the insert 104, or can be extend only partially around the circumference of the insert 104. Additionally, although FIG. 2B shows grooves 206 on both the inner surface 124 and outer surface 126 of the insert 104, the grooves 206 can alternatively be localized to certain portions of the insert 104, such as on the inner surface 124 only, on the outer surface 126 only, at or near the distal end 128 of the insert 104, at or near the proximal end 130 of the insert 104, at an intermediate region of the insert 104 that is spaced apart from the distal end 128 and/or proximal end 130, etc. Moreover, although FIG. 2B shows a series of horizontal grooves 206 in other embodiments, the grooves 206 can be arranged in a different pattern (e.g., vertical, angled) or can be randomly distributed.

Figure 2C:
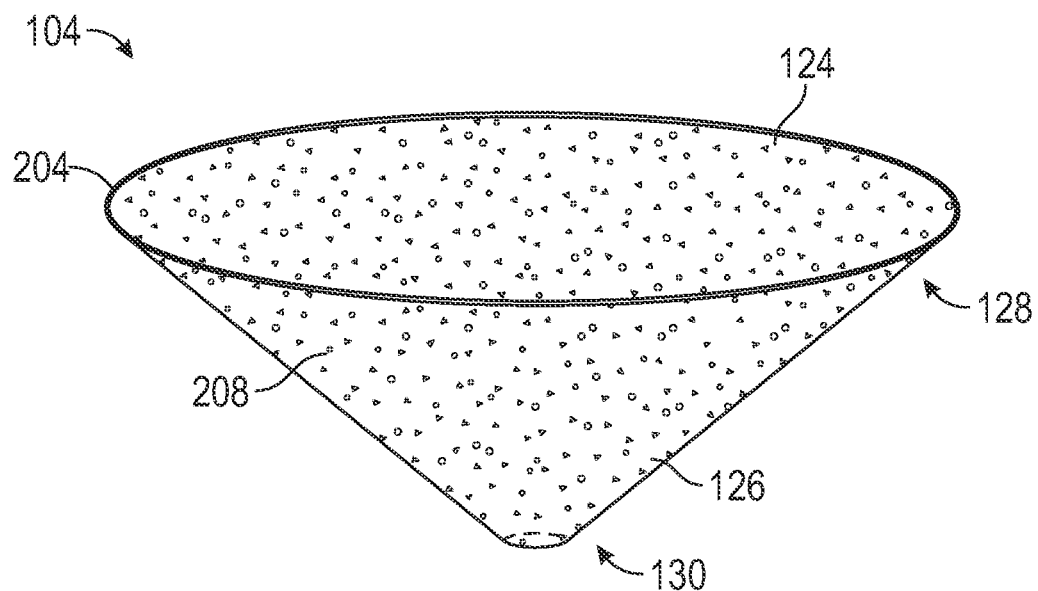
FIG. 2C is a perspective view of an insert including texturing, in accordance with embodiments of the present technology.

FIG. 2C is a perspective view of an insert 104 including texturing 208 configured to promote thrombosis, in accordance with embodiments of the present technology. The texturing 208 can be formed in a substrate 204 (e.g., a continuous material such as a film, strip, sheet, membrane, etc.) via etching, abrading, or other suitable techniques that increase the surface roughness of the substrate 204. Alternatively, the substrate 204 itself can be made of a relatively rough material, such that no additional process steps are needed to form the texturing 208. Although FIG. 2C shows uniform texturing 208 on both the inner surface 124 and outer surface 126 of the insert 104, the texturing 208 can alternatively be localized to certain portions of the insert 104, such as on the inner surface 124 only, on the outer surface 126 only, at or near the distal end 128 of the insert 104, at or near the proximal end 130 of the insert 104, at an intermediate region of the insert 104 that is spaced apart from the distal end 128 and/or proximal end 130, etc.

Figure 2D:
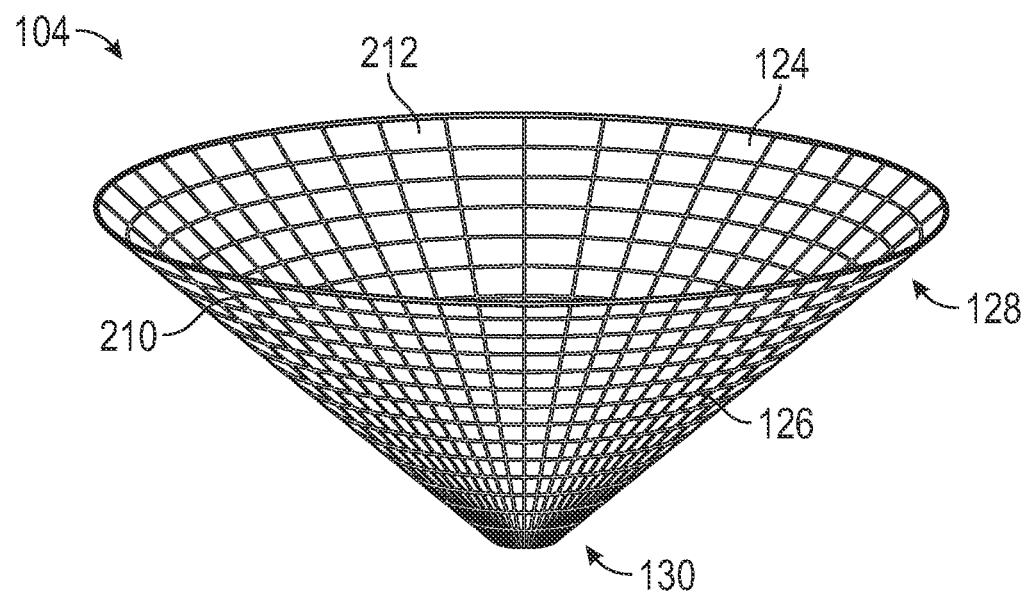
FIG. 2D is a perspective view of an insert formed from a plurality of filaments, in accordance with embodiments of the present technology.

FIG. 2D is a perspective view of an insert 104 formed from a mesh including a plurality of filaments 210, in accordance with embodiments of the present technology. In some embodiments, the insert 104 is a braid and the filaments 210 are woven or braided together. Alternatively, the insert 104 can be a stent and the filaments 210 can be laser-cut struts. As shown in FIG. 2D, the insert 104 includes a plurality of gaps 212 between the individual filaments 210. The presence of filaments 210 interspersed with gaps 212 can disrupt blood flow through and around the insert 104, thus promoting thrombogenesis. The filaments 210 can have any suitable size, such as a diameter within a range from 0.0004 inches to 0.0020 inches, or from 0.0009 inches to 0.0012 inches. For example, some or all of the filaments 210 can have a diameter of no more than 0.0004 inches, 0.0005 inches, 0.0006 inches, 0.0007 inches, 0.0008 inches, 0.0009 inches, 0.001 inches, 0.0011 inches, 0.0012 inches, 0.0013 inches, 0.0014 inches, 0.0015 inches, 0.0016 inches, 0.0017 inches, 0.0018 inches, 0.0019 inches, or 0.0020 inches. Some or all of the filaments 210 can have the same diameter, or some or all of the filaments 210 can have different cross-sectional diameters.

Figure 3A:
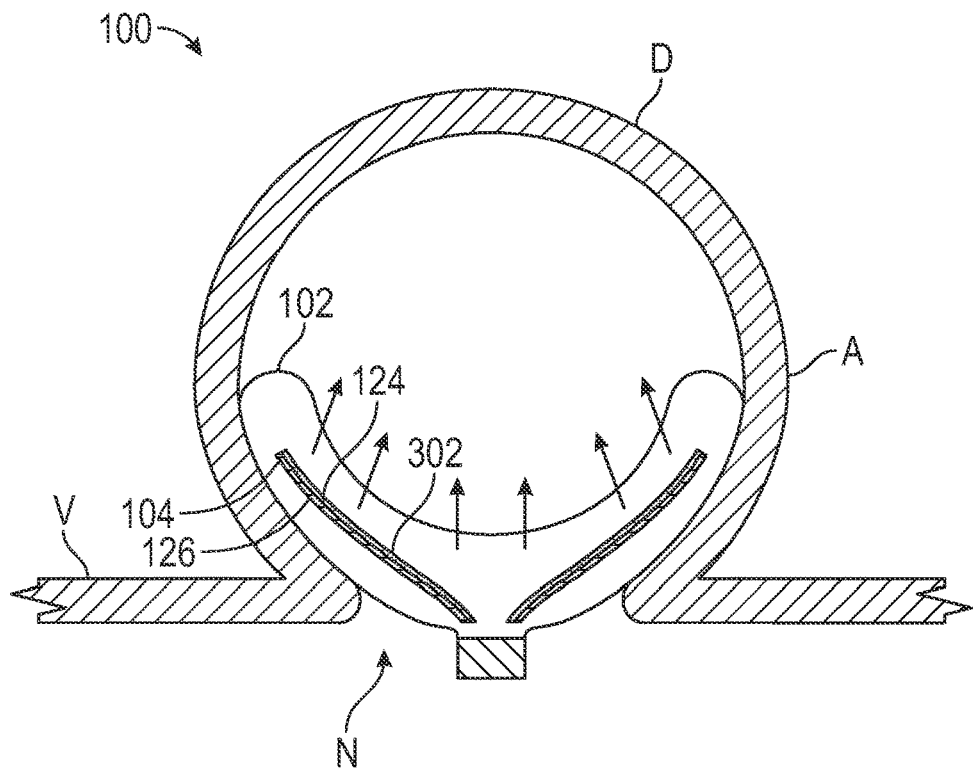
FIG. 3A is a side cross-sectional view of an occlusive device including an insert with an inner coating, in accordance with embodiments of the present technology.
Figure 3B:
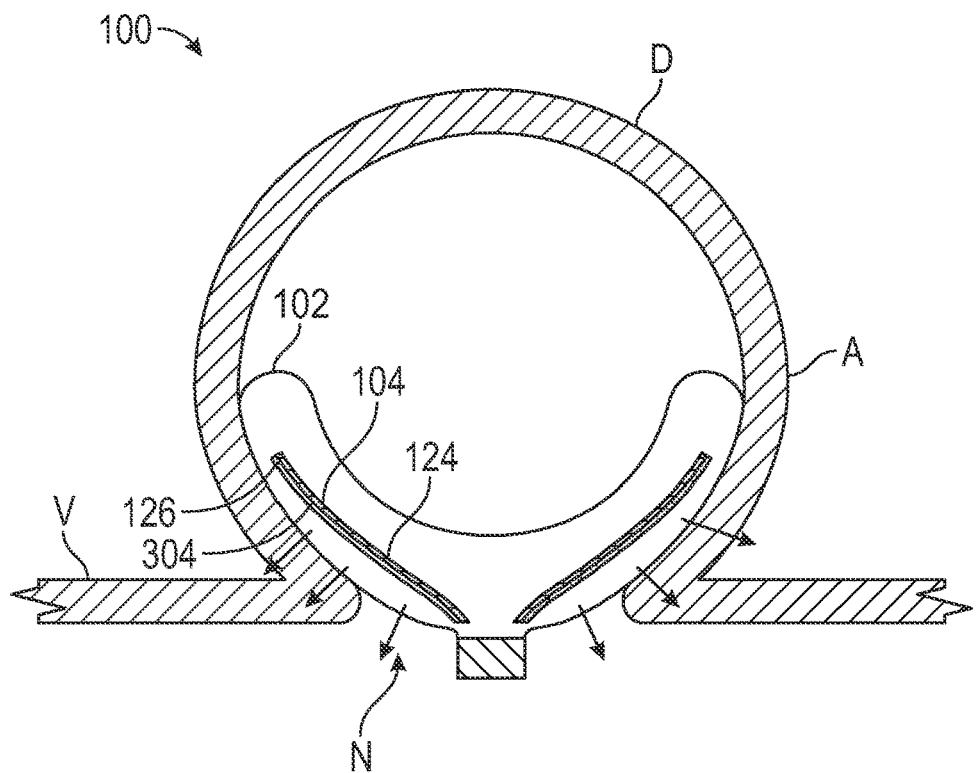
FIG. 3B is a side cross-sectional view of an occlusive device including an insert with an outer coating, in accordance with embodiments of the present technology.
Figure 3C:
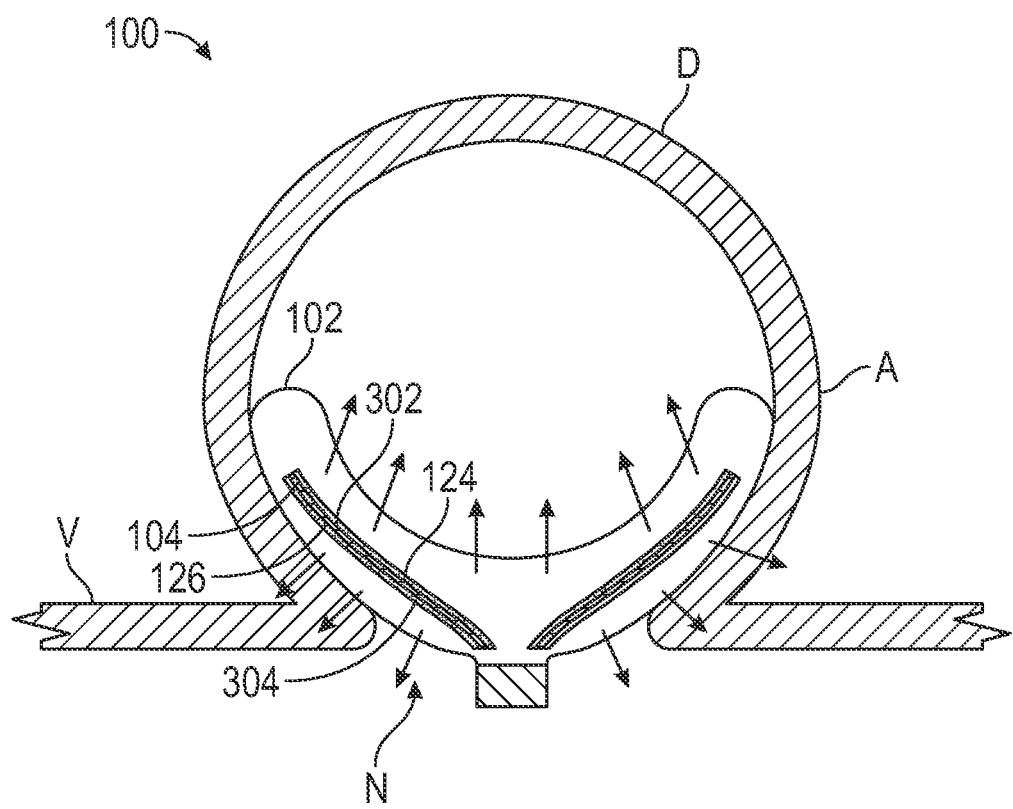
FIG. 3C is a side cross-sectional view of an occlusive device including an insert with an inner coating and an outer coating, in accordance with embodiments of the present technology.

FIGS. 3A-3C illustrate representative examples of controlled release coatings that may be incorporated into the insert 104 of the device 100 of FIGS. 1A-1D, in accordance with embodiments of the present technology. Any of the embodiments described in connection with FIGS. 3A-3C can be combined with each other and/or incorporated into any of the devices described herein.

FIG. 3A is a side cross-sectional view of a device 100 including an insert 104 with a coating 302 on the inner surface 124 of the insert 104 ("inner coating 302"), in accordance with embodiments of the present technology. The inner coating 302 is configured to release at least one active agent into the surrounding environment, such as a pharmaceutical compound, protein, peptide, antibody, nucleic acid, cell, particle, etc. For example, the active agent can be or include a thrombogenic agent, such as a thrombogenic material (e.g., in particulate form), coagulation factor, anti-fibrinolytic agent, or a combination thereof. As shown in FIG. 3A, because the flared shape of the insert 104 causes the inner surface 124 of the insert 104 to be oriented generally toward the dome D of the aneurysm A, the active agent contained in the inner coating 302 can elute primarily in a distal direction toward the aneurysm dome D and away from the aneurysm neck N. In embodiments where the active agent is a thrombogenic agent, this configuration can be advantageous for ensuring that thrombogenesis occurs primarily or entirely within the cavity of the aneurysm, rather than near or within the parent vessel V.

Although FIG. 3A illustrates a single inner coating 302, in other embodiments, the insert 104 can include multiple coatings 302 on the inner surface 124, such as two, three, four, five, or more layers of inner coatings 302. Some or all of the inner coatings 302 can include the same active agent, or some or all of the inner coatings 302 can include different active agents. Optionally, some of the inner coatings 302 may not include any active agent, and can instead serve other functions (e.g., enhancing adhesion of other coating layers, providing protection against damage, etc.). The outer surface 126 of the insert 104 can remain uncoated, or can also include one or more coatings, as discussed further below.

FIG. 3B is a side cross-sectional view of a device 100 including an insert 104 with a coating 304 on the outer surface 126 of the insert 104 ("outer coating 304"), in accordance with embodiments of the present technology. The outer coating 304 is configured to release at least one active agent into the surrounding environment, such as a pharmaceutical compound, protein, peptide, antibody, nucleic acid, cell, particle, etc. For example, the active agent can be or include an agent that inhibits thrombogenesis (e.g., heparin, albumin, direct thrombin inhibitors, anti-platelet agents, urokinase, t-PA) and/or promotes endothelialization and/or healing (e.g., EGF, RGD peptide). As shown in FIG. 3B, because the flared shape of the insert 104 causes the outer surface 126 of the insert 104 to be oriented generally toward the neck N of the aneurysm A, the active agent contained in the outer coating 302 can elute primarily in a proximal direction toward the aneurysm neck N and away from the aneurysm dome D. In embodiments where the active agent is an anti-thrombogenic, endothelialization, and/or healing agent, this configuration can be advantageous for preventing thrombosis in the parent vessel V and/or promoting endothelialization and/or healing across the neck N of the aneurysm.

Although FIG. 3B illustrates a single outer coating 304, in other embodiments, the insert 104 can include multiple coatings 304 on the outer surface 126, such as two, three, four, five, or more layers of outer coatings 304. Some or all of the outer coatings 304 can include the same active agent, or some or all of the outer coatings 304 can include different active agents. Optionally, some of the outer coatings 304 may not include any active agent, and can instead serve other functions (e.g., enhancing adhesion of other coating layers, providing protection against damage, etc.). The inner surface 124 of the insert 104 can remain uncoated, or can also include one or more coatings, as described above.

FIG. 3C is a side cross-sectional view of a device 100 including an insert 104 with both an inner coating 302 and an outer coating 304. Each of the coatings 302, 304 is configured to release at least one respective active agent into the surrounding environment. In some embodiments, the inner coating 302 is configured to release the same active agent(s) as the outer coating 304, e.g., both coatings 302, 304 release a thrombogenic agent. Alternatively, the inner coating 302 can release a different active agent or agents than the outer coating 304, e.g., the inner coating 302 releases a thrombogenic agent while the outer coating 304 releases an anti-thrombogenic, endothelialization, and/or healing agent. Accordingly, the insert 104 can promote occlusion of the aneurysm sac, while concurrently facilitating healing of the aneurysm neck to inhibit recanalization. Although FIG. 3C illustrates a single inner coating 302 and a single outer coating 304, in other embodiments, the insert 104 can include multiple coatings on the inner surface 124 and/or outer surface 126, as previously described.

The controlled release coatings described herein can be fabricated in various ways. For example, any of the coatings herein can include at least one active agent mixed with at least one polymeric material configured to mediate release of the active agent. In some embodiments, the active agent is released as the polymeric material degrades within the physiological environment of the aneurysm. Alternatively or in combination, the polymeric material can include pores, interstices, spaces, etc., that enable the active agent to elute out over time, with or without degradation of the polymeric material itself. Examples of suitable polymeric materials include, but are not limited to, BioLinx® (Medtronic), poly(vinyl alcohol), poly(ethylene-vinyl acetate), polyurethane, polycaprolactone, polyglycolic acid, polylactic acid, poly(lactide-co-glycolide), poly(ethylene oxide), poly(vinyl pyrrolidone), silicone, a silicone-urethane copolymer, an acrylic polymer, an acrylic-acrylonitrile copolymer, a latex polymer, or combinations thereof. Optionally, the coating can include the active agent by itself without any polymeric material. The coatings disclosed herein can be applied to the insert 104 using any suitable technique, such as dip coating, spraying coating, spin coating, adsorption, deposition, covalent bonding via a degradable crosslinker, etc.

Alternatively or in combination, the insert 104 itself can be made partially or entirely of a bulk material configured to provide controlled release of at least one active agent. The bulk material can include the active agent(s) mixed with a polymeric material, such as any of the materials described above in connection with controlled release coatings. In some embodiments, the bulk material is a degradable material, such that the insert 104 breaks down over time after implantation in the aneurysm. In other embodiments, the bulk material can be a nondegradable material, such that the insert 104 remains permanently within the aneurysm.

The insert 104 can be configured to provide controlled release of any suitable number of active agents, such as one, two, three, four, five, or more different active agents. The active agent(s) can be continuously released within the aneurysm over any suitable time period, such as a time period of at least 1 hour, 2 hours, 4 hours, 12 hours, 1 day, 2 days, 3 days, 4 days, 5 days, 6 days, 1 week, 2 weeks, 3 weeks, 4 weeks, 1 month, 2 months, 3 months, 6 months, or a year. The timing of the controlled release can be tuned based on factors such as the type of polymeric material used, the type of active agent(s) used, the amount of the active agent(s), the geometry of the insert 104, the thickness of the coating(s) and/or bulk material, or combinations thereof.

Figure 4A:
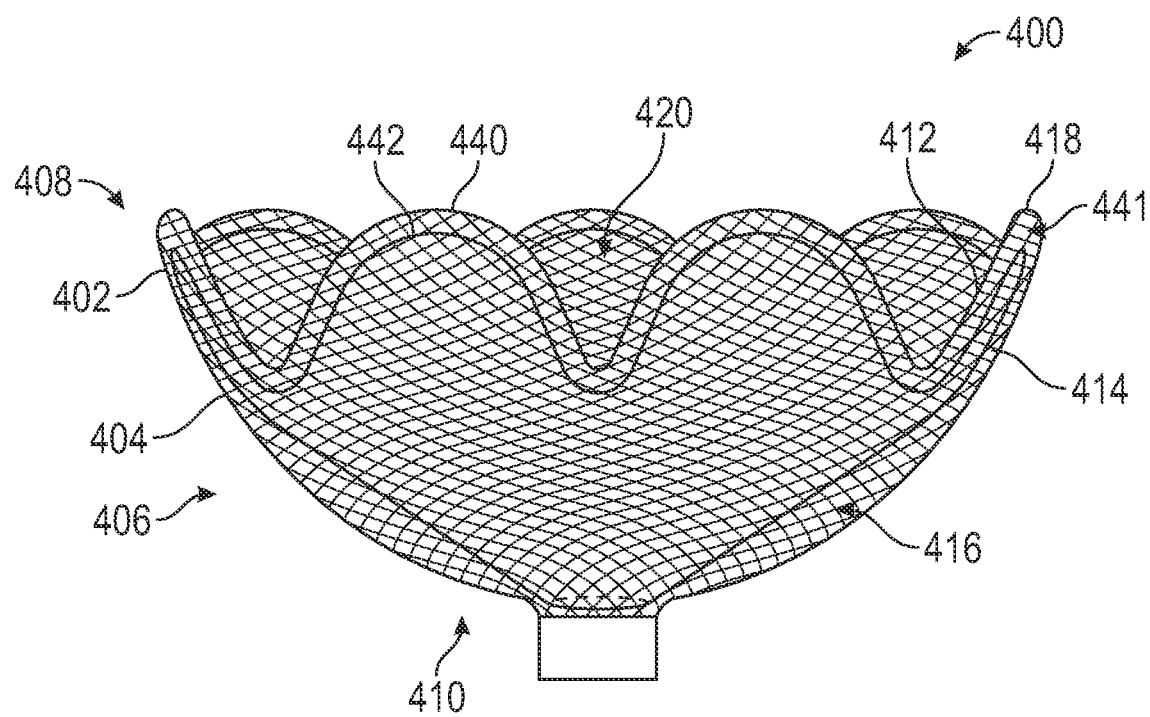
FIG. 4A is a perspective view of another occlusive device, in accordance with embodiments of the present technology.
Figure 4B:
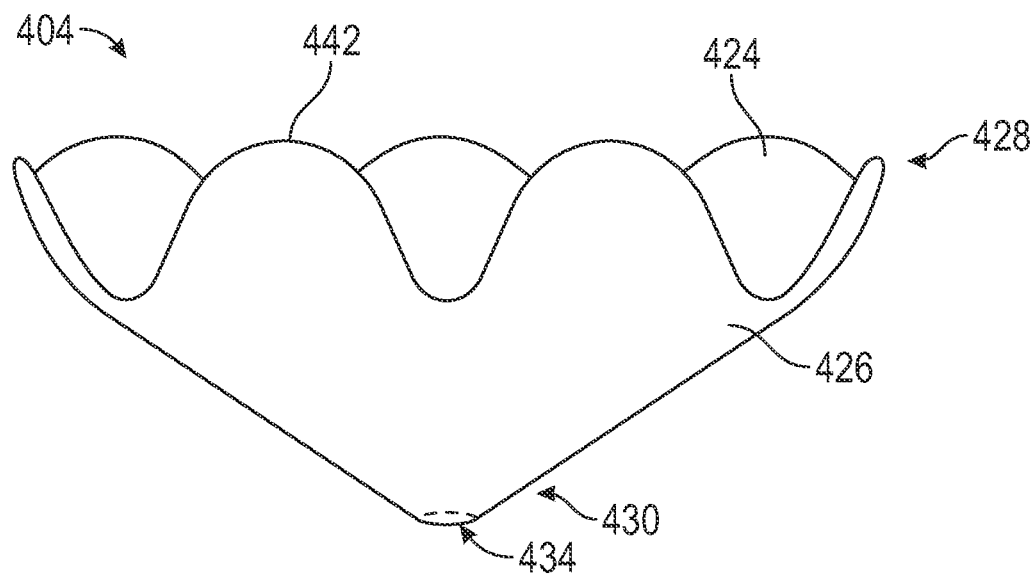
FIG. 4B is a perspective view of an insert of the occlusive device of FIG. 4A.

FIGS. 4A and 4B illustrate another occlusive device 400 ("device 400") configured in accordance with embodiments of the present technology. The device 400 can be generally similar to the device 100 of FIGS. 1A-1D. Accordingly, like numbers (e.g., mesh 102 versus mesh 402) are used to identify similar or identical structures, and discussion of the device 400 of FIGS. 4A and 4B will be limited to those features that differ from the device 100 of FIGS. 1A-1D. Additionally, any of the features of the devices 100 and 400 described herein can be combined with each other.

Referring to FIG. 4A, which illustrates a perspective view of the device 400, the device 400 includes a mesh 402 having an annular, bowl-shaped body 406 configured to be positioned within the aneurysm sac, a distal portion 408 configured to be oriented toward the aneurysm dome, and a proximal portion 410 configured to cover the aneurysm neck. In the illustrated embodiment, the distal portion 408 of the mesh 402 has an undulating shape defining a plurality of petals 440 ("mesh petals 440"). Stated differently, the distal end of the upper wall 412 of the mesh 402, the distal end of the lower wall 414 of the mesh 402, and the fold region 418 connecting the upper wall 412 and lower wall 414 can collectively define the structure of each mesh petal 440. The distal end of the upper wall 412 and the distal end of the lower wall 414 can be separated by a gap, such that each mesh petal 440 is a hollow structure defining a distal end sub-cavity 441 that is connected to the internal cavity 416 of the mesh 402. The mesh petals 440 can be peaks, flanges, protrusions, etc., that surround the cavity 420 of the mesh 402 to facilitate retention of an embolization element within the cavity 420. Although FIG. 4A illustrates the mesh 402 as having seven mesh petals 440, the mesh 402 can alternatively have a different number of mesh petals 440, such as two, three, four, five, six, eight, nine, ten, or more mesh petals 440.

As best seen in FIG. 4B, which shows a perspective view of the insert 404 of the device 400, the distal end 428 of the insert 404 can also include a respective plurality of petals 442 ("insert petals 442") surrounding the distal aperture 432 of the insert 404. In the illustrated embodiment, the insert petals 442 are configured similarly to the mesh petals 440 (e.g., with respect to shape, size, number, and/or location). Accordingly, when the insert 404 is positioned within the mesh 402 (FIG. 4A), each insert petal 442 is aligned with and/or received at least partially within the distal end sub-cavity 441 of a corresponding mesh petal 440. In other embodiments, however, the insert 404 can include a different number of petals than the mesh 402. For example, although the insert 404 is depicted as having seven insert petals 442, the insert 404 can alternatively have two, three, four, five, six, eight, nine, ten, or more petals 442. Additionally, some or all of the insert petals 442 can be circumferentially offset from the mesh petals 440. Optionally, the insert 404 can have a different shape than the mesh 402. For example, the mesh 402 can include petals 440 while the insert 404 does not include any petals (e.g., similar to the insert 104 of FIGS. 1A-1D), or the insert 404 can include petals 442 while the mesh 402 does not include any petals (e.g., similar to the mesh 102 of FIGS. 1A and 1B).

FIGS. 5A-5E illustrate a method of treating an aneurysm with an occlusive device, in accordance with embodiments of the present technology. Although the illustrated embodiment is shown and described in terms of the device 100 of FIGS. 1A-1D, the method can be applied to any embodiment of the occlusive devices described herein (e.g., the device 400 of FIGS. 4A and 4B).

Figure 5A:
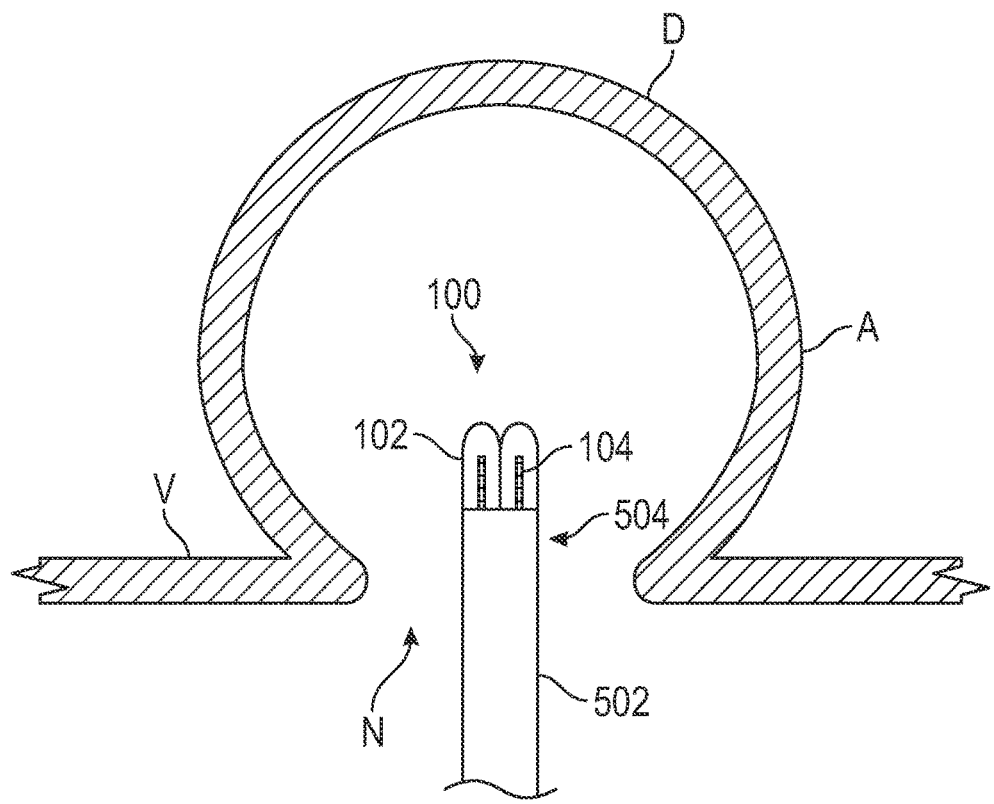
FIG. 5A is a side cross-sectional view of an occlusive device being introduced into an aneurysm, in accordance with embodiments of the present technology.

Referring first to FIG. 5A, the device 100 can be loaded within a first elongate shaft 502 (e.g., a delivery catheter such as a microcatheter) in a low-profile configuration. When in the low-profile configuration, the mesh 102 and insert 104 of the device 100 can be compressed, flattened, or otherwise compacted in a generally linear configuration to conform to the interior lumen of the first elongate shaft 502.

The device 100 can then be intravascularly delivered to a location within a blood vessel V adjacent a target aneurysm A via the first elongate shaft 502. As shown in FIG. 2A, a distal tip 504 of the first elongate shaft 502 can be advanced through the neck N of the aneurysm A and into an interior cavity of the aneurysm A. The device 100 can then be deployed by pushing the device 100 distally through the opening in the distal tip 504 of the first elongate shaft 502 and into the aneurysm cavity, e.g., using a pusher member (not shown) coupled to the hub 122 of the device 100.

Figure 5B:
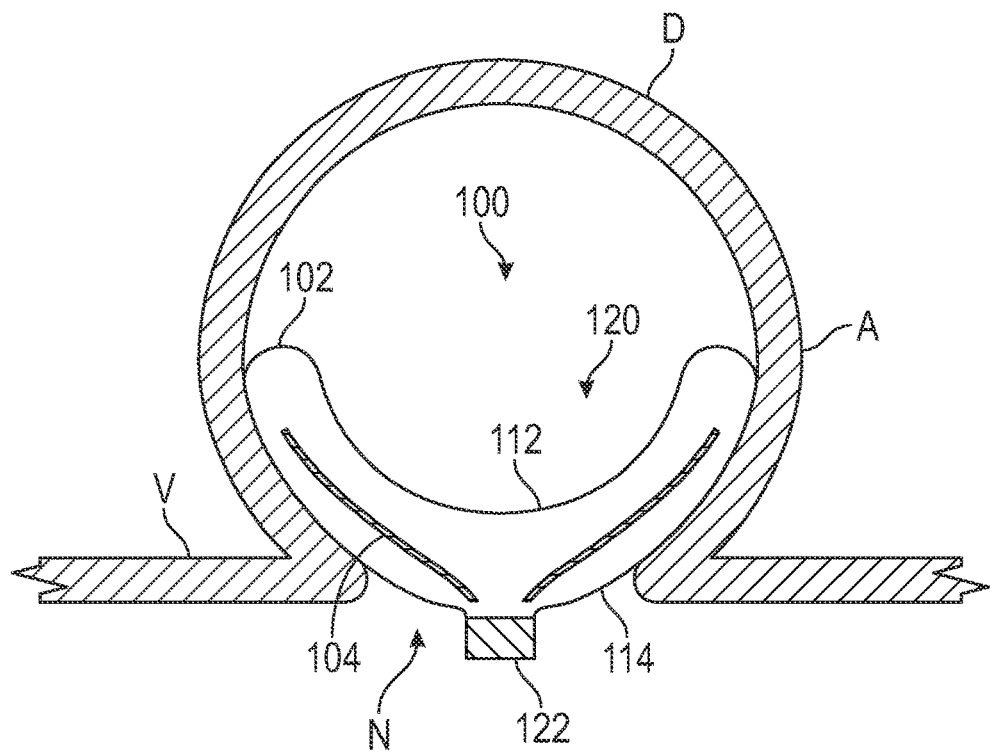
FIG. 5B is a side cross-sectional view of the occlusive device of FIG. 5A after deployment in the aneurysm.

Referring next to FIG. 5B, as the device 100 exits the first elongate shaft 502, the mesh 102 can self-expand from the low-profile configuration into the expanded configuration. The self-expansion forces from the mesh 102 can push the insert 104 into its expanded configuration, or the insert 104 can also self-expand when released from the constraints of the first elongate shaft 502. As shown in FIG. 5B, in the expanded configuration, the upper wall 112 and cavity 120 of the mesh 102 face the dome D of the aneurysm A, while the lower wall 114 of the mesh 102 contacts the interior surface of the aneurysm A and bridges the neck N. Once the device 100 is deployed, the hub 122 can be detached from the pusher member, and the pusher member and first elongate shaft 502 can then be withdrawn from the aneurysm A.

Figure 5C:
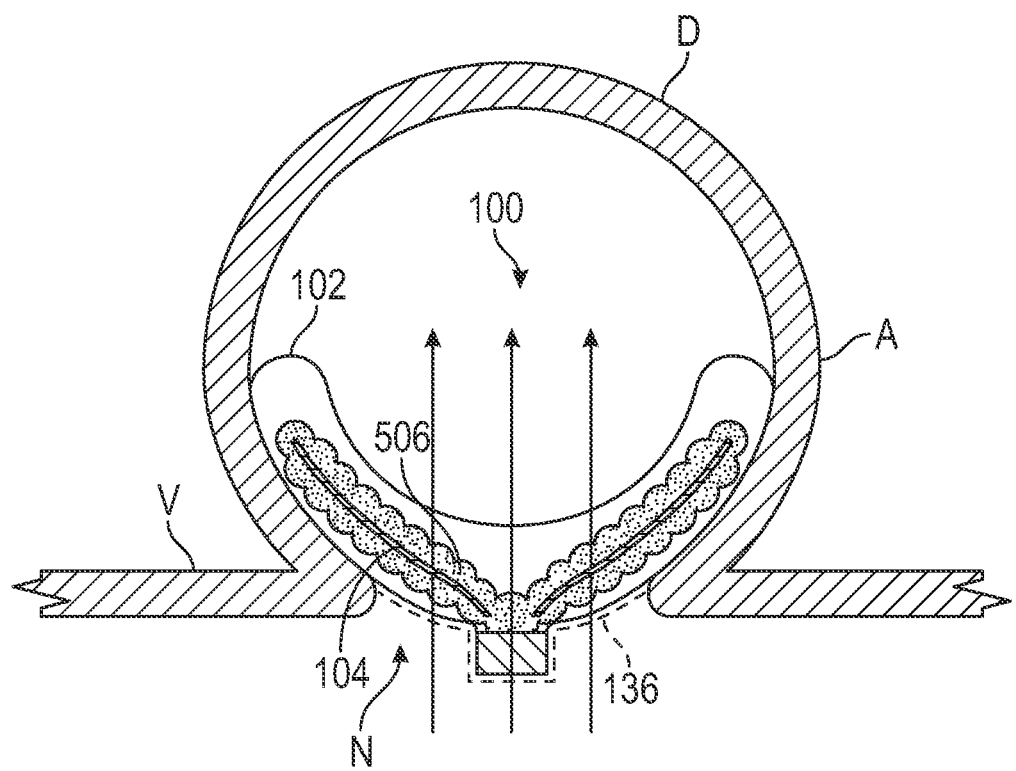
FIG. 5C is a side cross-sectional view of thrombus formation on an insert of the occlusive device of FIG. 5B.

Referring next to FIG. 5C, blood entering the aneurysm A from the parent vessel V interacts with the thrombogenic feature(s) of the insert 104, resulting in formation of thrombus 506 on and/or near the insert 104. As previously described, the thrombogenic feature(s) can include any of the following: (a) a physical structure that increases the surface area of the insert 104 and/or disrupts blood flow near the insert 104, such as any of the embodiments of FIGS. 2A-2D; (b) a thrombogenic material used to form all or a portion of the insert 104, such as ePTFE or CoCr; and/or (c) a releasable thrombogenic agent incorporated into the insert 104, e.g., in accordance with the embodiments of FIGS. 3A-3C. Optionally, the device 100 can include an anti-thrombogenic coating 136 on components that protrude into the parent vessel V, such as the proximal portion of the mesh 102 and/or the hub 122.

Figure 5D:
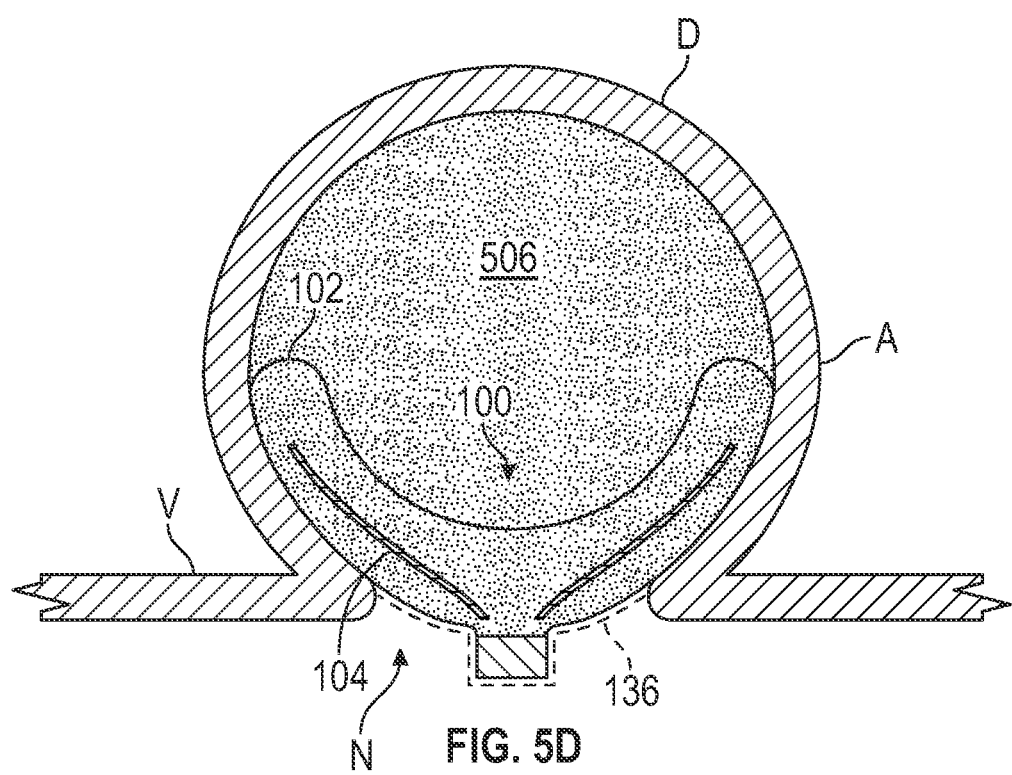
FIG. 5D is a side cross-sectional view of the aneurysm occluded by thrombus and the occlusive device of FIG. 5B.

Referring next to FIG. 5D, the thrombogenic feature(s) of the insert 104 can promote hemostasis and/or coagulation within the aneurysm A until most or all of the cavity is filled with thrombus 506. The portions of the device 100 including the anti-thrombogenic coating 136 can remain partially or completely free of thrombus 506, thus providing an exposed substrate for growth of an endothelial layer.

Figure 5E:
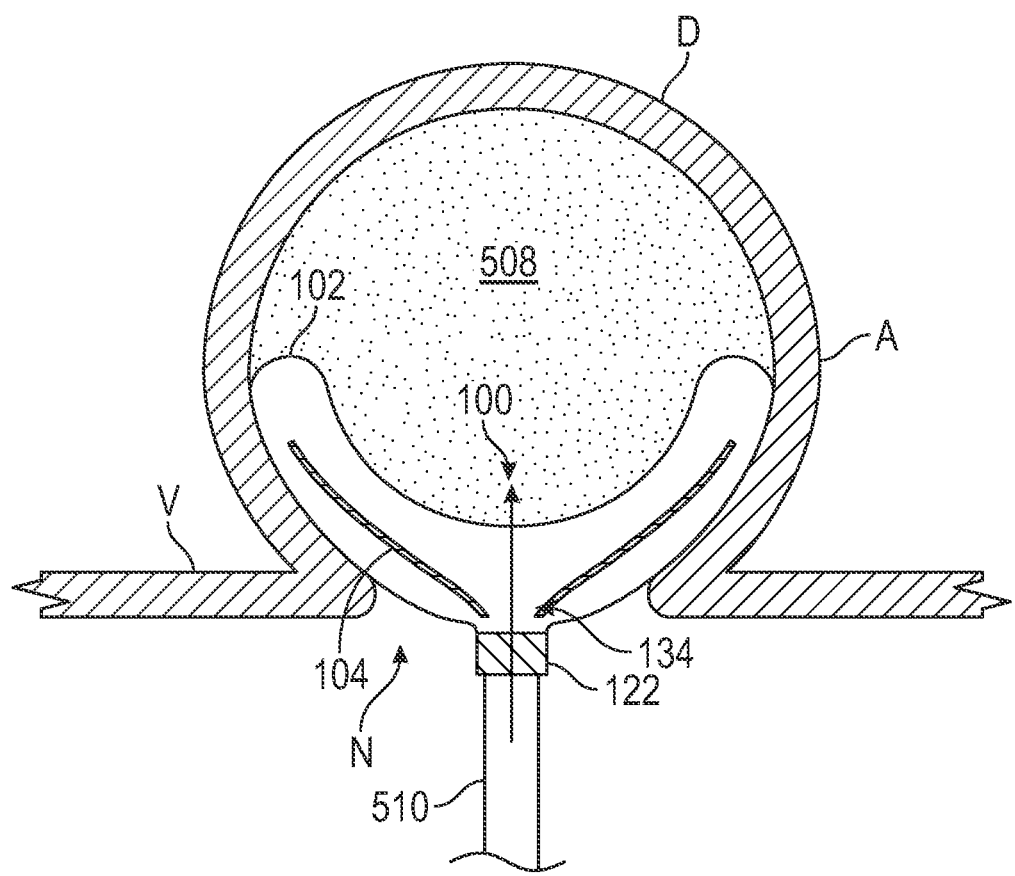
FIG. 5E is a side cross-sectional view of the aneurysm occluded by a liquid embolic and the occlusive device of FIG. 5B.

Referring next to FIG. 5E, the device 100 can optionally be used in combination with an embolization element, such as a liquid embolic 508. The liquid embolic 508 can be introduced into the aneurysm A via a second elongate shaft 510 coupled to the hub 122. The second elongate shaft 510 can be received within the first elongate shaft 502 (not shown in FIG. 5E) and advanced to the aneurysm A together with the device 100. After the device 100 is deployed, the liquid embolic 508 is pumped into the aneurysm cavity through the second elongate shaft 510, and passes through the hub 122, the proximal aperture 134 in the insert 104, and the mesh 102, and into the interior of the aneurysm A. Subsequently, the second elongate shaft 510 can be decoupled from the hub 122 and withdrawn, leaving the device 100 and liquid embolic 508 in place. The thrombogenic feature(s) of the insert 104 can function in concert with the liquid embolic 508 to occlude the interior of the aneurysm A.

Alternatively, the second elongate shaft 510 can be a separate component that is not coupled to the hub 122, but is instead introduced into the aneurysm A before the device 100 is deployed. When the device 100 is subsequently deployed, the mesh 102 can expand to push the second elongate shaft 510 outwardly toward the side of the aneurysm A to hold the second elongate shaft 510 in place between the mesh 102 and the inner surface of the aneurysm A. The liquid embolic 508 (or other embolization element, such as a coil) can then be introduced into the aneurysm A via the second elongate shaft 510.

CONCLUSION

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as for parent vessel take down, endovascular aneurysms outside of the brain, arterial-venous malformations, embolization, atrial and ventricular septal defects, patent ductus arteriosus, and patent foramen ovale. Additionally, several other embodiments of the technology can have different states, components, or procedures than those described herein. It will be appreciated that specific elements, substructures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1A-5E.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. An occlusive device for treating an aneurysm, the occlusive device comprising:
    an expandable mesh configured to span a neck of the aneurysm, the expandable mesh comprising an upper wall and a lower wall, wherein an internal cavity is defined between the upper wall and the lower wall, and wherein the expandable mesh comprises an anti-thrombogenic coating localized to a portion of the lower wall of the expandable mesh; and
    an insert positioned within the internal cavity of the expandable mesh between the upper wall and the lower wall, the insert comprising a film having an inner surface and an outer surface, wherein the inner surface of the film faces the upper wall of the expandable mesh, and the outer surface of the film faces the lower wall of the expandable mesh and wherein the insert comprises an open upper end defining an aperture,
    wherein the insert is configured to promote thrombosis within the aneurysm and the anti-thrombogenic coating is configured to discourage thrombosis across the neck of the aneurysm when the occlusive device is deployed within the aneurysm, and
    wherein when the occlusive device is deployed within the aneurysm, the expandable mesh forms a bowl structure comprising a distal portion, a proximal portion, and the internal cavity extending from the distal portion toward the proximal portion.

2. The occlusive device of claim 1, wherein, when the occlusive device is deployed within the aneurysm, the insert comprises a flared shape comprising a proximal end, and a distal end wider than the proximal end.

3. The occlusive device of claim 1, wherein the insert comprises a polymeric material, a metallic material, or a combination thereof.

4. The occlusive device of claim 1, wherein the insert defines a plurality of pores extending between the inner surface and the outer surface of the film, and wherein the plurality of pores are configured to enhance thrombogenicity of the insert.

5. The occlusive device of claim 1, wherein the insert comprises texturing on one or more of the inner surface or the outer surface of the film, and wherein the texturing is configured to enhance thrombogenicity of the insert.

6. The occlusive device of claim 1, wherein the insert is configured to release at least one active agent into the aneurysm.

7. The occlusive device of claim 6, wherein the at least one active agent is configured to promote thrombosis within the aneurysm.

8. An occlusive device for treating an aneurysm, the occlusive device comprising:
    a mesh configured to self-expand into a bowl structure, the mesh including a distal layer and a proximal layer, wherein the distal layer comprises a concave surface defining a cavity of the bowl structure; and
    an insert positioned between the distal layer and the proximal layer, wherein the insert comprises a membrane having an outer surface and an inner surface, wherein the insert comprises an open distal end defining an aperture, and wherein the insert comprises at least one thrombogenic feature.

9. The occlusive device of claim 8, further comprising a coating on a portion of the proximal layer of the mesh, wherein the coating is configured to reduce thrombogenesis on the portion of the proximal layer.

10. The occlusive device of claim 8, wherein the outer surface of the membrane is oriented toward the proximal layer of the mesh, and the inner surface of the membrane is oriented toward the distal layer of the mesh.

11. The occlusive device of claim 8, wherein the insert comprises a flared shape comprising a proximal end that is narrower than the distal end.

12. The occlusive device of claim 11, wherein the narrower proximal end of the insert defines a proximal aperture configured to allow material to pass therethrough.

13. The occlusive device of claim 8, wherein the at least one thrombogenic feature comprises one or more of a thrombogenic material, a plurality of pores, texturing on one or more of the inner surface or the outer surface of the membrane, a plurality of filaments, or a releasable agent.

14. An occlusive device for treating an aneurysm, the occlusive device comprising:
    an expandable mesh configured to span a neck of the aneurysm, the expandable mesh comprising a distal wall and a proximal wall, wherein when the occlusive device is deployed within the aneurysm, the expandable mesh forms a bowl structure comprising the distal wall, the proximal wall, and an internal cavity between the distal wall and proximal wall; and
    an insert positioned in the internal cavity, wherein the insert is formed from a single material layer having an inner surface and an outer surface, wherein the insert comprises an open distal end defining an aperture, and wherein the insert includes at least one thrombogenic feature.

15. The occlusive device of claim 14, wherein the insert comprises a mesh.

16. The occlusive device of claim 14, wherein the single material layer comprises a thrombogenic material, and the at least one thrombogenic feature comprises the thrombogenic material.

17. The occlusive device of claim 14, wherein the at least one thrombogenic feature comprises a physical structure formed in the single material layer of the insert, wherein the physical structure comprises pores, texturing, protrusions, indentations, or a combination thereof.

18. The occlusive device of claim 14, wherein the at least one thrombogenic feature comprises a releasable thrombogenic agent.

19. The occlusive device of claim 18, wherein the releasable thrombogenic agent is (a) incorporated into a coating on one or more of the inner surface or the outer surface of the single material layer, (b) incorporated into the single material layer of the insert, or (c) both (a) and (b).

* * * * *